United States Patent
Ito

(10) Patent No.: US 10,344,697 B2
(45) Date of Patent: Jul. 9, 2019

(54) CONTROL APPARATUS FOR INTERNAL COMBUSTION ENGINE

(71) Applicant: TOYOTA JIDOSHA KABUSHIKI KAISHA, Toyota-shi, Aichi-ken (JP)

(72) Inventor: Hironori Ito, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 183 days.

(21) Appl. No.: 15/632,999

(22) Filed: Jun. 26, 2017

(65) Prior Publication Data

US 2017/0370314 A1 Dec. 28, 2017

(30) Foreign Application Priority Data

Jun. 28, 2016 (JP) .................................. 2016-127651

(51) Int. Cl.
*G01N 33/00* (2006.01)
*F02D 41/14* (2006.01)
(Continued)

(52) U.S. Cl.
CPC ......... *F02D 41/146* (2013.01); *F01N 3/0878* (2013.01); *F01N 3/2053* (2013.01);
(Continued)

(58) Field of Classification Search
CPC ............... F01N 3/0878; F01N 3/2053; F01N 2560/028; F02D 41/1479; F02D 41/146; F02D 41/222; F02D 41/2414; F02D 41/144; F02D 41/0065; F02D 2200/0418; F02D 2200/0414; G01N 33/007; G01N 27/121; G01N 27/223; G01N 27/605; F02M 35/10393

See application file for complete search history.

(56) References Cited

U.S. PATENT DOCUMENTS 5,792,938 A 8/1998 Gokhfeld
2003/0046979 A1 3/2003 Yamazaki et al.
(Continued)

FOREIGN PATENT DOCUMENTS

JP S58-074846 A 5/1983
JP 2001-507799 A 6/2001
(Continued)

*Primary Examiner* — Blake A Tankersley
(74) *Attorney, Agent, or Firm* — Hunton Andrews Kurth LLP

(57) ABSTRACT

An internal combustion engine has a humidity sensor that is disposed in an intake passage of the internal combustion engine, a temperature sensor configured to detect an intake air temperature in a position of the humidity sensor, and a controller configured to correct an offset error of the sensor value by adding a correction value to the sensor value. The controller is configured to acquire the intake air temperatures respectively at a plurality of timings in a process of the intake air temperature changing, acquire the sensor values at the respective plurality of timings, calculate values excluding influences of temperature differences of the intake air temperatures from the respective sensor values as humidity index values respectively, and determine a correction value so that a variation degree of the humidity index values becomes small.

9 Claims, 12 Drawing Sheets

(51) Int. Cl.
*F01N 3/08* (2006.01)
*F01N 3/20* (2006.01)
*F01P 3/20* (2006.01)
*F02D 41/24* (2006.01)
*F02D 41/00* (2006.01)

(52) U.S. Cl.
CPC ............ *F01P 3/20* (2013.01); *F02D 41/1479* (2013.01); *F02D 41/2474* (2013.01); *G01N 33/007* (2013.01); *F01N 2560/028* (2013.01); *F02D 41/0065* (2013.01); *F02D 41/144* (2013.01); *F02D 2200/0414* (2013.01); *F02D 2200/0418* (2013.01)

(56) References Cited

U.S. PATENT DOCUMENTS

| | | | | |
|---|---|---|---|---|
| 2003/0115943 A1* | 6/2003 | Ueno | .................... | F01N 3/0814 73/114.73 |
| 2005/0072404 A1* | 4/2005 | Cullen | ................ | F02D 41/1475 123/399 |
| 2014/0338644 A1* | 11/2014 | MacNeille | .............. | F02D 37/02 123/568.22 |

FOREIGN PATENT DOCUMENTS

| | | |
|---|---|---|
| JP | 2002-048010 A | 2/2002 |
| JP | 2003-148135 A | 5/2003 |
| JP | 2005-062199 A | 3/2005 |
| JP | 2014-085154 A | 5/2014 |
| JP | 2015-206328 A | 11/2015 |

* cited by examiner

CONTROL APPARATUS FOR INTERNAL COMBUSTION ENGINE

CROSS-REFERENCE TO RELATED APPLICATION

The present application claims priority to Japanese Patent Application No. 2016-127651 filed on Jun. 28, 2016, which is incorporated herein by reference in its entirety.

FIELD

The present disclosure relates to a control apparatus for an internal combustion engine, and particularly relates to a control apparatus for an internal combustion engine including a humidity sensor.

BACKGROUND

Conventionally, there has been disclosed a device that adjusts a NOx value of exhaust gas by controlling humidity of intake air of an internal combustion engine based on absolute humidity, for example, in Patent Literature 1. In this device, absolute humidity is calculated from relative humidity that is detected by a humidity sensor and a temperature of intake air that is detected by a temperature sensor. Subsequently, the opening degree of a humidity adjustment damper provided at an intake duct that feeds highly humid air is adjusted so that the calculated absolute humidity becomes a target value.

Following is a list of patent literatures which the applicant has noticed as background arts of embodiments the present disclosure.

Patent Literature 1: JP 2002-048010 A
Patent Literature 2: JP 2003-148135 A

SUMMARY

A humidity sensor detects the relative humidity of outside air by using the fact that the amount of water adsorbed by a humidity sensitive film varies in accordance with a change in the humidity of outside air. Consequently, when the humidity sensitive film adsorbs substances other than water, for example, exhaust gas or organic substances in the atmosphere due to degradation over time or the like, an offset error occurs to the relative humidity detected by the humidity sensor. Consequently, in the configuration in which a humidity sensor is disposed in the intake passage of an internal combustion engine, and the relative humidity of intake air flowing in the intake passage is used in control of the internal combustion engine, it is desired to construct a device for correcting an error of the relative humidity which is detected, on board.

The present disclosure is made in the light of the problem as described above, and has an object to provide a control apparatus for an internal combustion engine capable of correcting an offset error of a sensor value of a humidity sensor that is disposed in an intake passage of the internal combustion engine.

In order to attain the above described object, the present disclosure is a control apparatus for an internal combustion engine including a humidity sensor that is disposed in an intake passage of the internal combustion engine, and is configured to detect a sensor value corresponding to relative humidity of intake air in the intake passage, a temperature sensor configured to detect an intake air temperature in a position of the humidity sensor, and a controller configured to correct an offset error of the sensor value by performing correction of adding a correction value to the sensor value. The controller is configured to acquire the intake air temperatures respectively at a plurality of timings in a process of the intake air temperature changing, acquire the sensor values at the respective plurality of timings, calculate respective values excluding influences of temperature differences of the intake air temperatures from the respective sensor values as humidity index values, and determine the correction value so that a variation degree of the humidity index values becomes small.

A second disclosure is, in a first disclosure, such that the controller is configured to calculate absolute humidity that is calculated by using the sensor value and the intake air temperature corresponding to the sensor value as the humidity index value.

A third disclosure is, in the first disclosure, such that the controller is configured to calculate relative humidity at a time of the intake air temperature being a predetermined reference intake air temperature as the humidity index value by using the sensor value.

A fourth disclosure is, in the first disclosure, such that the controller is configured to determine the correction value so that a variance value of the humidity index values becomes minimum.

A fifth disclosure is, in the first disclosure, such that, the controller is configured to acquire a first sensor value that is the sensor value at a time of the intake air temperature being a first intake air temperature, and a second sensor value that is the sensor value at a time of the intake air temperature changing from the first intake air temperature and reaching a second intake air temperature, calculate values excluding an influence of a temperature difference of the first intake air temperature and the second intake air temperature from the first sensor value and the second sensor value, as a first humidity index value and a second humidity index value respectively, and determine the correction value so that a difference value of the first humidity index value and the second humidity index value is close to zero.

A sixth disclosure is, in the first disclosure, such that, the controller is configured to calculate relative humidity differences to reference absolute humidity from the sensor values as the humidity index values, and calculate the reference absolute humidity at which the variation degree of the relative humidity differences becomes minimum, and determine an average value of the relative humidity differences at the calculated reference absolute humidity as the correction value.

A seventh disclosure is, in the first disclosure, such that the controller is configured to restrict acquisition of the sensor value, until an integrated value of a volume of intake air that is taken into the intake passage after start of the internal combustion engine exceeds a capacity from an inlet to the humidity sensor in the intake passage, in a warm-up period of the internal combustion engine.

An eighth disclosure is, in the first disclosure, such that the controller is configured to restrict acquisition of the sensor value, when intake air containing a fuel component flows in the position of the humidity sensor in the intake passage of the internal combustion engine.

Under a condition in which the absolute humidity of intake air in the intake passage is constant, the sensor value which is detected by the humidity sensor changes in accordance with the intake air temperature in the intake passage at each time. According to the first disclosure, at a plurality of timings in the process of the intake air temperature changing, a plurality of sensor values with different intake air temperatures are acquired. Subsequently, the humidity index values that are the values excluding the influences of the intake air temperature differences from these sensor values are respectively calculated, and the correction value is determined so that the variation degree of these humidity index values becomes small. When the sensor value of the humidity sensor is a true value under the condition in which the absolute humidity of the intake air in the intake passage is constant, the humidity index value is kept at a fixed value even when the intake air temperature changes. According to the present disclosure, the correction value is determined so that the variation degree of the humidity index values becomes small, and therefore it becomes possible to bring the relative humidity acquired by the humidity sensor close to the true value.

According to the second disclosure, the absolute humidity as the humidity index value is calculated by using the intake air temperature and the sensor value. Under the condition in which the absolute humidity of the intake air in the intake passage is constant, the absolute humidity does not change even when the intake air temperature changes. Consequently, according to the present disclosure, the influences of the intake air temperature differences can be excluded from a plurality of relative humidities with different intake air temperatures.

According to the third disclosure, the relative humidity in the case of the intake air temperature being the reference intake air temperature is calculated as the humidity index value by using the intake air temperature and the sensor value. Consequently, according to the present disclosure, the influences of the intake air temperature differences can be excluded from the plurality of sensor values with different intake air temperatures.

According to the fourth disclosure, the correction value is determined so that the variance value of the humidity index values becomes minimum, and therefore it becomes possible to determine the correction value so that the variation degree of the humidity index values becomes minimum.

According to the fifth disclosure, two sensor values with different intake air temperatures can be compared after the influence of the temperature difference is excluded. Consequently, according to the present disclosure, it becomes possible to correct the error of the sensor value of the humidity sensor with high precision by determining the correction value so that the difference value is close to zero.

According to the sixth disclosure, the relative humidity differences from the sensor values to the reference absolute humidity are calculated as the humidity index values, and the reference absolute humidity at which the variation of the relative humidity differences becomes minimum is calculated. The reference absolute humidity at which the variation of the relative humidity differences becomes minimum expresses absolute humidity that is the closest to the true value. Consequently, according to the present disclosure, it becomes possible to correct the error of the sensor value of the humidity sensor with high precision by determining the average value of the relative humidity differences at the reference absolute humidity as the correction value.

It is conceivable that the inside of the intake passage before start of the internal combustion engine differs from outside air in humidity. According to the seventh disclosure, the sensor value before the outside air that is taken in after start of the internal combustion engine reaches the humidity sensor can be prevented from being used, and therefore it becomes possible to restrain erroneous correction of the humidity sensor.

According to the eighth disclosure, the sensor value in the case of the intake air containing a fuel component flowing in the position of the humidity sensor in the intake passage can be prevented from being used, and therefore it becomes possible to restrain erroneous correction of the humidity sensor by use of the sensor value of the air different from outside air.

DETAILED DESCRIPTION

First Embodiment

Hereinafter, a first embodiment of the present disclosure will be described with reference to the drawings.

1-1. System Configuration of First Embodiment of the Present Disclosure

Figure 1:
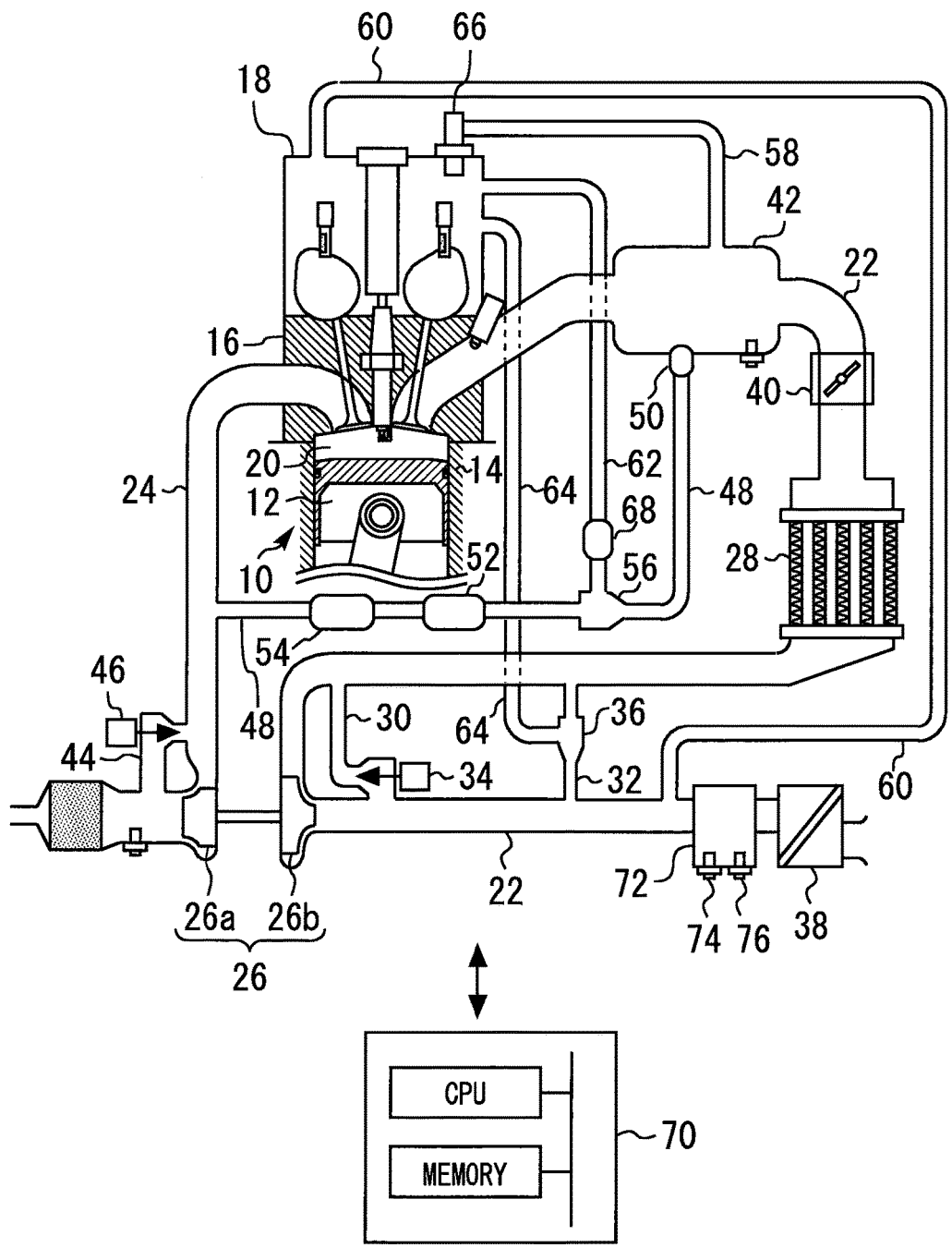
FIG. 1 is a diagram illustrating a system configuration of a first embodiment.

FIG. 1 is a diagram illustrating a system configuration of the first embodiment. As illustrated in FIG. 1, a system of the present embodiment includes an engine 10 as an internal combustion engine. The number of cylinders and cylinder disposition of the engine 10 are not specially limited. The engine 10 includes a cylinder block 14 having a piston 12 inside. A cylinder head 16 is assembled to an upper portion of the cylinder block 14. The cylinder head 16 is covered with a cylinder head cover 18. A space from a top surface of the piston 12 to the cylinder head 16 forms a combustion chamber 20. The cylinder head 16 includes an intake passage 22 and an exhaust passage 24 that communicate with the combustion chamber 20.

Further, the system of the present embodiment includes a supercharger 26. The supercharger 26 includes a turbine 26a that is provided in the exhaust passage 24, and a compressor 26b that is provided in the intake passage 22. The turbine 26a and the compressor 26b are connected to each other. At a time of operation of the supercharger 26, the compressor 26b is driven by the turbine 26a that rotates by receiving an exhaust pressure, and intake air is compressed and supercharged by the compressor 26b.

In the intake passage 22, an intercooler 28 that cools intake air that is supercharged by the compressor 26b is provided. In the intake passage 22 at an upstream side of the intercooler 28, air bypass passages 30 and 32 that bypass the compressor 26b are provided. In the air bypass passage 30, an ABV (Air Bypass Valve) 34 is provided. By opening the ABV 34, abrupt rise of a supercharging pressure is prevented. In the air bypass passage 32, an ejector 36 for introducing intake air in a PCV passage 64 into the air bypass passage 32 is provided. Further, in the intake passage 22 at an upstream side of the compressor 26b, an air cleaner 38 is provided. Meanwhile, in the intake passage 22 at a downstream side of the intercooler 28, an electronically controlled type throttle valve 40 is provided. In the intake passage 22 at a downstream side of the throttle valve 40, a surge tank 42 is provided.

In the intake passage 22 that is at the upstream side of the compressor 26b and at a downstream side of the air cleaner 38, an air flow meter 72 for detecting an intake air amount is provided. In the air flow meter 72, a temperature sensor 74 that detects a temperature of intake air and a humidity sensor 76 that detects humidity of the intake air are contained. Note that the temperature sensor 74 and the humidity sensor 76 may be configured separately from the air flow meter 72. Details of the humidity sensor 76 will be described later.

In the exhaust passage 24, an exhaust bypass passage 44 that bypasses the turbine 26a is provided. In the exhaust bypass passage 44, an electromagnetically driven type WGV (Waste Gate Valve) 46 is provided. Back pressure can be adjusted by opening the WGV 46, and therefore, a pump loss of the engine and an in-cylinder residual amount of exhaust gas are suppressed.

Further, the system of the present embodiment is loaded with an EGR mechanism that recirculates exhaust gas to the intake passage 22 from the exhaust passage 24. The EGR mechanism includes an EGR passage 48 that connects the exhaust passage 24 at an upstream side of the turbine 26a, and the surge tank 42. On the EGR passage 48, an EGR valve 50 that adjusts an EGR gas amount, a water cooling type EGR cooler 52, and an EGR catalyst 54 are provided. The EGR valve 50 is disposed at a position nearest to the surge tank 42, and the EGR catalyst 54 is disposed at a position near to the exhaust passage 24. Further, the EGR mechanism includes an ejector 56 between the EGR valve 50 and the EGR cooler 52. The ejector 56 is for introducing gas in a PCV passage 62 to the EGR passage 48.

Further, the system of the present embodiment includes a blowby gas reducing mechanism that reduces blowby gas. Blowby gas refers to gas that flows into a crankcase from a gap between the piston 12 and a cylinder wall surface, which is gas including unburned fuel and oil mist. The blowby gas reducing mechanism includes four kinds of PCV passages 58, 60, 62 and 64. The PCV passage 58 connects the cylinder head cover 18 and the surge tank 42. On the PCV passage 58, a PCV valve 66 is provided. The PCV passage 60 connects the cylinder head cover 18 and the intake passage 22 at an upstream side from the compressor 26b. The PCV passage 62 connects a suction port of the ejector 56, and the cylinder head cover 18. On the PCV passage 62, a PCV valve 68 is provided. The PCV passage 64 connects a suction port of the ejector 36 and the cylinder head cover 18.

In addition, the system of the present embodiment includes an ECU (Electronic Control Unit) 70. The ECU 70 includes at least an input/output interface, a memory and a CPU (a processor). The input/output interface is provided to take in sensor signals from various sensors that are mounted to the internal combustion engine, and output operation signals to actuators included by the internal combustion engine. The sensors from which the ECU 70 takes in signals include various sensors necessary to control the engine 10, such as a throttle opening degree sensor that detects an opening degree of the throttle valve 40, and a temperature sensor that detects a cooling water temperature of the engine 10. The actuators to which the ECU outputs operation signals include various actuators such as the ABV 34, the throttle valve 40, the WGV 46 and the EGR valve 50. In the memory, various control programs for controlling the internal combustion engine, maps and the like are stored. The CPU (processor) reads the control program or the like from the memory and executes the control program, and generates an operation signal based on the sensor signals which are taken in.

1-2. Configuration of Humidity Sensor

Figure 2:
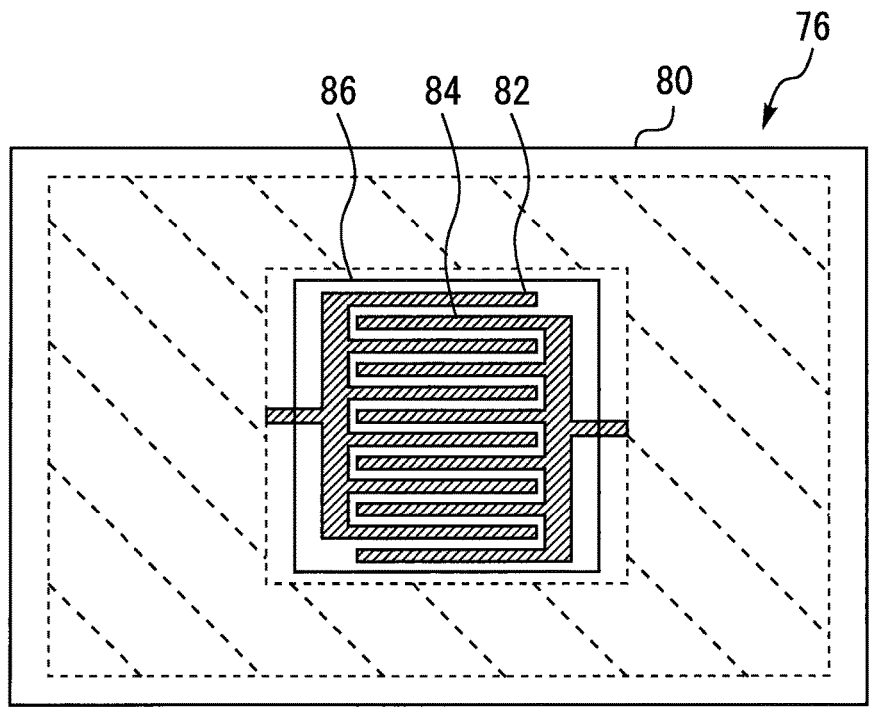
FIG. 2 is a view illustrating a schematic plan view of a humidity sensor that is used in the system of the first embodiment.

FIG. 2 is a view illustrating a schematic plan view of a humidity sensor 76 that is used in the system of the present embodiment. The humidity sensor 76 is an electrical capacitance type humidity sensor, and outputs a sensor signal corresponding to relative humidity. The humidity sensor 76 is configured mainly by a silicon substrate 80, detecting electrodes 82 and 84, and a humidity sensitive film 86. An insulation film is formed on the silicon substrate 80, and on the insulation film, the comb-like detecting electrodes 82 and 84 are disposed to oppose to be meshed with each other. Further, the humidity sensitive film 86 is a film with an electrical capacitance value changing in accordance with humidity, and is disposed over the silicon substrate 80 in such a manner as to cover the detecting electrodes 82 and 84. When water molecules enter the film of the humidity sensitive film 86, a dielectric constant of the humidity sensitive film 86 greatly changes in accordance with an amount of water that enters therein. Accordingly, relative humidity around the sensor can be detected by detecting a change of a capacitance value between the detecting electrodes 82 and 84 as a sensor signal. Note that the humidity sensor 76 is not limited to an electrical capacitance type humidity sensor, but may be configured as another humidity sensor of an electrical resistance type or the like.

1-3. Operation of System of First Embodiment

Figure 3:
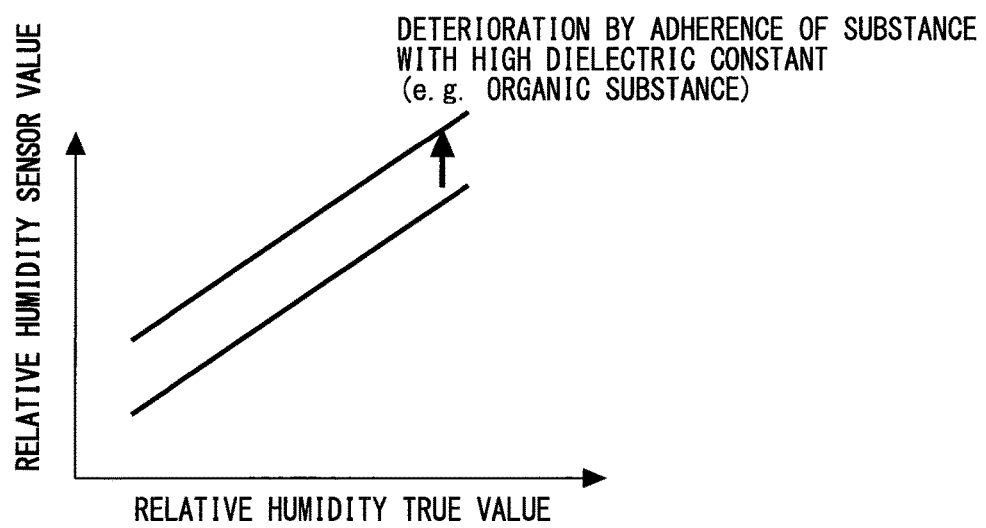
FIG. 3 is a diagram illustrating a relation between a sensor value of relative humidity and a true value of the relative humidity.

As described above, the humidity sensor 76 detects relative humidity of outside air by using the fact that an amount of water adsorbed by the humidity sensitive film 86 changes in accordance with a change in humidity of outside air. Consequently, when the humidity sensitive film 86 adsorbs substances other than water, for example, exhaust gas and organic substances in the atmosphere, an error is superimposed on the relative humidity which is detected. FIG. 3 is a diagram illustrating a relationship between a sensor value of relative humidity and a true value of the relative humidity. Note that the sensor value of the relative humidity mentioned here refers to relative humidity that is calculated from the sensor signal of the humidity sensor 76. As illustrated in FIG. 3, when deterioration caused by substances with a high dielectric constant adhering to the humidity sensitive film 86 occurs, an offset error that is a sensor value corresponding to the true value of relative humidity being offset to a high humidity side occurs. Like this, the humidity sensor 76 has a possibility that a detection characteristic thereof changes due to a surrounding environment, degradation over time and the like. Consequently, in order to keep detection precision of the humidity sensor 76, it is demanded to learn the offset error that is superimposed on the sensor value of the humidity sensor 76 disposed in the intake passage 22 and correct the offset error.

However, the sensor value of the relative humidity changes in accordance with a change in the intake air temperature. Consequently, even if the sensor values of the relative humidity under different intake air temperature conditions are simply compared, the offset error of the humidity sensor 76 cannot be determined. Thus, in the system of the first embodiment, the offset error of the humidity sensor 76 disposed in the intake passage 22 of the engine 10 is determined by using a detection method shown as follows.

1-3-1. Correction of Offset Error of Humidity Sensor

Figure 4:
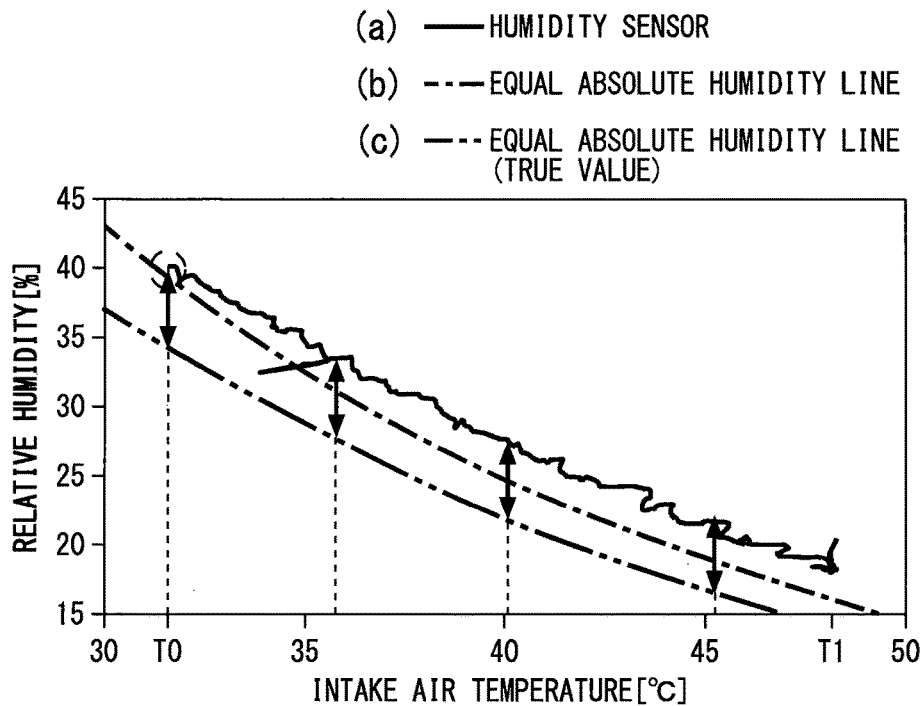
FIG. 4 is a diagram for explaining a method for correcting an offset error of the humidity sensor.

FIG. 4 is a diagram for explaining a method for correcting the offset error of the humidity sensor 76. A solid line shown by (a) in FIG. 4 represents a change in relative humidity detected by the humidity sensor 76 in a warm-up period of the engine 10. Further, an alternate long and short dash line shown by (b) in FIG. 4 represents an equal absolute humidity line of absolute humidity that is converted from the sensor value of the humidity sensor 76 at a time point in an initial period of warm-up of the engine 10 (a time point at which the intake air temperature is T0 in FIG. 4). Further, a two-dot chain line shown by (c) in FIG. 4 represents an equal absolute humidity line corresponding to the true value of relative humidity of intake air. Note that the warm-up period mentioned here means a period in which a temperature in an engine compartment is rising with a rise in a water temperature and an oil temperature, after cold start of the engine 10, or the like.

When it is assumed that intake air with equal absolute humidity continues to flow in the warm-up period of the engine 10, a theoretical value of the relative humidity transitions on the equal absolute humidity line shown by (b) in FIG. 4 with rise of the intake air temperature. Consequently, when the relative humidity detected by the humidity sensor 76 gradually deviates from the relative humidity on the equal absolute humidity line shown by (b) in FIG. 4 as warm-up of the engine 10 advances, it is highly likely that an offset error is superimposed on the sensor value of the humidity sensor 76.

The equal absolute humidity line in the case of the offset error being superimposed on the sensor value of the humidity sensor 76 becomes a line obtained by offsetting the equal absolute humidity line of the true value by a fixed amount. Consequently, if an error amount corresponding to the offset amount is determined and is added to the sensor value, the relative humidity that is detected by the humidity sensor 76 can be brought close to the true value.

However, as described above, the relative humidity of intake air changes in accordance with the intake air temperature. Consequently, even if relative humidities at different intake air temperatures are directly compared, the offset error cannot be determined. In contrast with this, in the absolute humidity that is calculated from the intake air temperature and the relative humidity, an influence of the intake air temperature difference is excluded, so that a variation degree of these values can be an index of an offset error amount that is superimposed on the sensor value.

Figure 5:
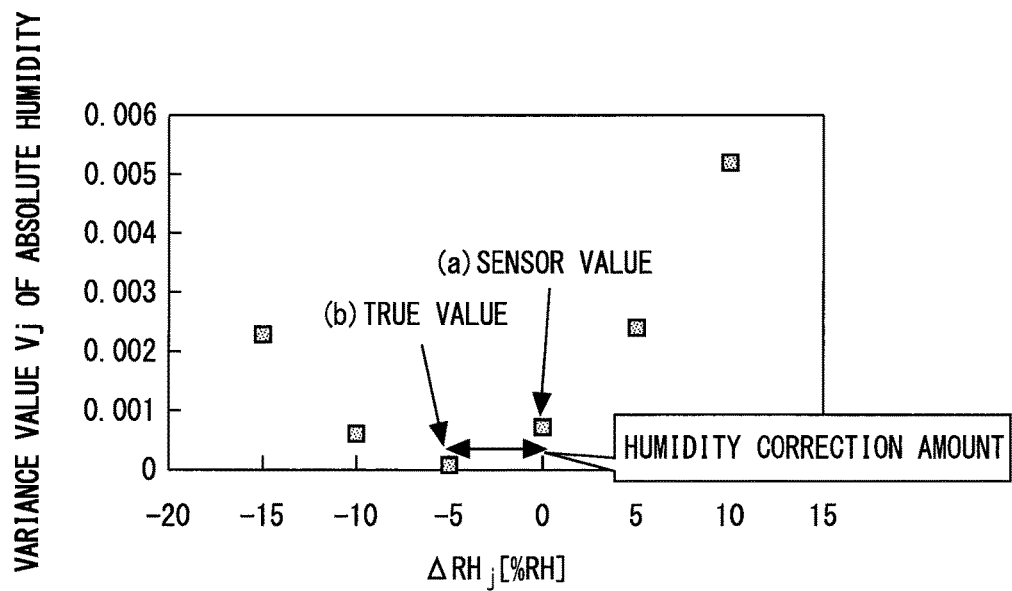
FIG. 5 is an example illustrating a relationship between $\Delta RHj$, and variance value $Vj$ of absolute humidity $AHi, j$.

Thus, in the system of the first embodiment of the present disclosure, relative humidity $RH_i$ at an intake air temperature $T_i$ ($i=1, 2, \ldots, n$) is each calculated, and from each relative humidity $RH_i$ which is calculated, absolute humidity $AH_i$ is calculated. A change amount $\Delta AH_{i,j}$ of the absolute humidity at a time of the relative humidity changing by $\Delta RH_j$ ($\Delta RH_j=0, \pm 5, \pm 10, \ldots$) at the intake air temperature $T_i$ is calculated, and a variance value $V_j$ of a value $AH_{i,j}$ obtained by adding the change amount $\Delta AH_{i,j}$ to the absolute humidity $AH_i$ is calculated. FIG. 5 is an example showing a relationship between $\Delta RH_j$ and the variance value $V_j$ of the absolute humidity $AH_{i,j}$. A point (a) illustrated in FIG. 5 represents the variance value $V_j$ ($\Delta RH_j=0$) in a case of using the sensor value. Since the variance value $V_j$ represents the variation degree of the absolute temperature, it can be determined that $\Delta RH_j$ ($\Delta RH_j=-5$ in this case) corresponding to a point (b) at which the variance value $V_j$ becomes minimum is a humidity correction amount with which the sensor value of the relative humidity is the closest to the true value. Accordingly, in the system of the first embodiment of the present disclosure, $\Delta RH_j$ with which the variance value $V_j$ becomes minimum is calculated, and correction of adding the calculated $\Delta RH_j$ to the relative humidity $RH_i$ which is the sensor value of the humidity sensor 76 is performed.

Figure 6:
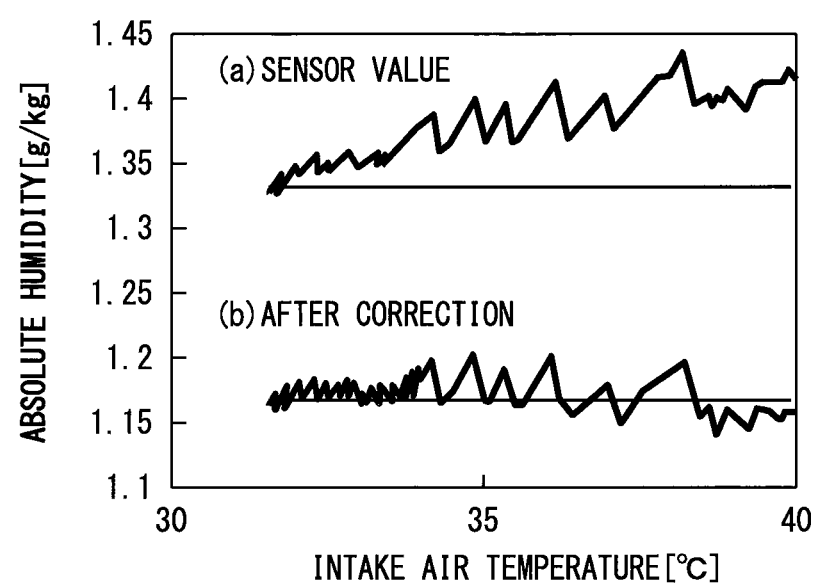
FIG. 6 is a diagram illustrating a change of absolute humidity with respect to an intake air temperature.

FIG. 6 is a diagram illustrating a change of the absolute humidity to the intake air temperature. In FIG. 6, (a) represents the absolute humidity which is calculated from the sensor value, and (b) in FIG. 6 represents absolute humidity after correction of the offset error. As is understandable from FIG. 6, according to the above described correction, the sensor value can be corrected so that the absolute humidity calculated from the sensor value of the humidity sensor 76 becomes constant as much as possible, and therefore it becomes possible to correct the offset error which is superimposed of the relative humidity with high precision.

1-4. Configuration for Realizing Offset Error Correction of Humidity Sensor

Figure 7:
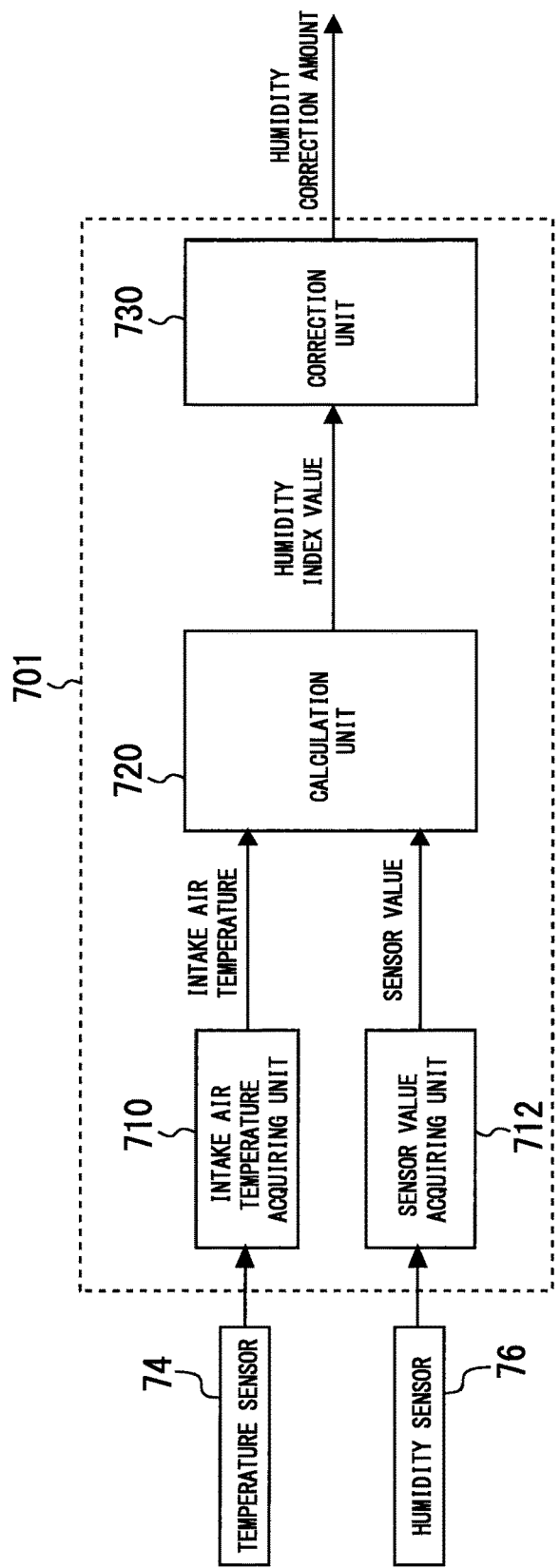
FIG. 7 is a functional block diagram illustrating a configuration of a controller that performs offset error correction of the humidity sensor.

Next, a specific configuration for realizing offset error correction of the humidity sensor 76 will be described. The offset error correction of the humidity sensor 76 is realized by a controller 701. FIG. 7 is a functional block diagram illustrating a configuration of the controller 701 that performs offset error correction of the humidity sensor 76. The controller 701 is a part of a processing circuitry of the ECU 70, and is for realizing a function for performing offset error correction of the humidity sensor 76.

The controller 701 is configured by an intake air temperature acquiring unit 710, a sensor value acquiring unit 712, a calculation unit 720 and a correction unit 730. The intake air temperature acquiring unit 710 acquires intake air temperatures by using the temperature sensor 74 at a plurality of timings in a process of the intake air temperature changing. The sensor value acquiring unit 712 acquires a sensor value (relative humidity) of the humidity sensor 76 at each of the above described plurality of timings. The calculation unit 720 receives inputs of the intake air temperatures and the sensor values at the above described plurality of timings, and calculates humidity index values excluding influences by the intake air temperature differences from these sensor values. The correction unit 730 determines a humidity correction amount that is added to the sensor values so that a variation degree of the respective humidity index values that are inputted becomes small.

In the offset error correction of the humidity sensor 76 described above, the intake air temperature in FIG. 7 corresponds to the intake air temperature $T_i$ ($i=1, 2, \ldots, n$), the sensor value corresponds to the relative humidity $RH_i$ ($i=1, 2, \ldots, n$), and the humidity index value corresponds to the absolute humidity $AH_i$.

Respective functions of the intake air temperature acquiring unit 710, the sensor value acquiring unit 712, the calculation unit 720 and the correction unit 730 in the controller 701 are realized by the processing circuitry. That is, the controller 701 includes the processing circuitry for acquiring the intake air temperatures by using the temperature sensor 74 at a plurality of timings in the process of the intake air temperature changing, acquiring the sensor value by using the humidity sensor 76 at each of the above described plurality of timings, receiving the inputs of the intake air temperatures and the sensor values at the above described plurality of timings, calculating the humidity index values from which the influences by the intake air temperature differences are excluded respectively, and determining the humidity correction amount which is added to the sensor values so that the variation degree of the respective humidity index values that are inputted becomes small. The processing circuitry is a CPU (Central Processing Unit, also referred to as a central processor, a processor unit, an arithmetic unit, a microprocessor, a microcomputer, a processor, and a DSP).

The functions of the intake air temperature acquiring unit 710, the sensor value acquiring unit 712, the calculation unit 720 and the correction unit 730 are realized by software, firmware, or a combination of software and firmware. The software and the firmware are described as programs, and are stored in a memory. The processing circuitry realizes the functions of the respective units by reading and executing the programs stored in the memory. That is, the controller 701 includes the memory for storing the program for resultantly executing a step of acquiring the intake air temperatures by using the temperature sensor 74 at a plurality of timings in the process of the intake air temperature changing, a step of acquiring the sensor value by using the humidity sensor 76 at each of the above described plurality of timings, a step of receiving the inputs of the intake air temperatures and the sensor values at the above described plurality of timings and calculating the humidity index values from which the influences by the intake air temperature differences are excluded from these sensor values respectively, and a step of determining the humidity correction amount so that the variation degree of the respective humidity index values that are inputted becomes small. Further, these programs can be said as the programs for causing a computer to execute procedures and methods of the intake air temperature acquiring unit 710, the sensor value acquiring unit 712, the calculation unit 720 and the correction unit 730. Here, to the memory, a nonvolatile or volatile semiconductor memory such as a RAM, a ROM, a flash memory, an EPROM, or an EPPROM is applicable.

1-5. Execution Conditions of Offset Error Correction of Humidity Sensor

In the aforementioned offset error correction of the humidity sensor, it becomes possible to enhance correction precision by satisfying the following conditions.

1-5-1. Condition for Intake Air Temperature to Change

In addition to the warm-up period of the engine 10 described above, the offset error correction of the humidity sensor can be executed if it is a situation where the intake air temperature changes. For example, in a soaking period from stop of the engine 10 to start of a next time, the intake air temperature drops, and therefore, the offset error correction of the humidity sensor can be executed.

An intake air temperature can be changed in a short time period by changing an air current from outside air to an inlet of the intake passage 22. For example, if turning-on-and-off of a fan of a radiator is switched, a temperature inside the engine compartment can be changed, and thereby the intake air temperature can be changed. Further, in an engine including an openable and closable grille, the intake air temperature can be also changed by opening and closing of the grille. Further, in an engine including a so-called hot air intake that introduces high-temperature intake air into the intake passage 22, the intake air temperature can be also changed by switching a change-over valve for switching introduction of the hot air intake. Furthermore, in an engine including a heat exchanger in a midpoint in the intake passage 22 or in the engine compartment, the intake air temperature can be also changed by operating the heat exchanger.

1-5-2. Condition for Ensuring Temperature Difference in Intake Air Temperature

When the temperature change of the intake air temperature is small, a large difference does not occur to the relative humidity which is detected, and therefore, it is difficult to determine whether or not an offset error is superimposed on the sensor signal of the humidity sensor. Consequently, the system of the first embodiment is configured to detect the sensor signal of the humidity sensor and the intake air temperature repeatedly until the temperature change of the intake air temperature becomes larger than a threshold value (for example, an error span of the detection value). According to the configuration like this, it becomes possible to determine a magnitude of the offset error of the humidity sensor with high precision.

1-5-3. Condition for Outside Air to Reach Humidity Sensor

When the engine 10 is started, the absolute humidity of air in the intake passage 22 and in the engine compartment before start is likely to be different from the absolute humidity of outside air at the time of start. Therefore, the system of the first embodiment is configured to restrict the offset error correction of the humidity sensor in a period until outside air reaches the humidity sensor 76 after start of the engine 10. In this configuration, the offset error correction of the humidity sensor may be restricted until an integrated value of a volume of an intake air amount after start of the engine 10 exceeds an intake capacity from the inlet of the intake passage 22 to a position where the humidity sensor 76 is disposed, for example. Further, in a case of such a configuration that air stays in the engine compartment, an air capacity of the engine compartment may be further taken into consideration. According to the configuration like this, an output signal after outside air reaches the humidity sensor can be used, and therefore, the offset error correction of the humidity sensor can be realized with high precision. Note that the determination of whether outside air reaches the humidity sensor 76 may be made in accordance with a time period after the time of start of the engine 10.

1-5-4. Case of Gas Containing Fuel Component Reaching Humidity Sensor

The engine 10 of the first embodiment includes the EGR mechanism and the blowby gas reducing mechanism. Consequently, under an operation condition in which the EGR gas and the blowby gas are recirculated to the intake passage 22, these combustion gases are assumed to reach the humidity sensor 76 by an influence of an intake air pulsating motion or the like. Thus, the system of the first embodiment is configured to restrict the offset error correction of the humidity sensor under the condition in which gas containing a fuel component such as the EGR gas and the blowby gas reaches the humidity sensor 76. According to the configuration like this, a normal output signal of the humidity sensor 76 can be used, and therefore, the offset error correction of the humidity sensor can be realized with high precision.

1-6. Specific Processing of System of First Embodiment

Figure 8:
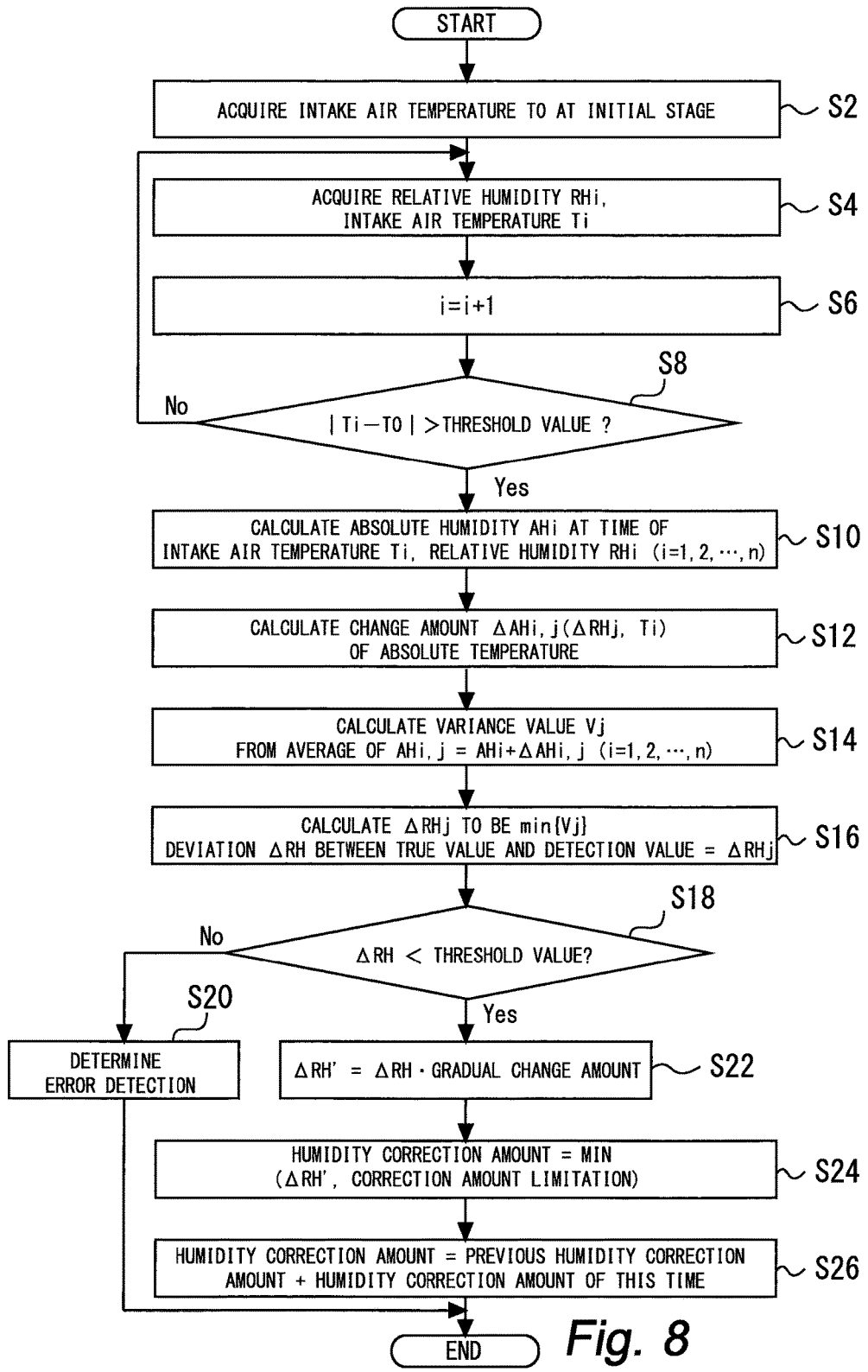
FIG. 8 is a flowchart of a routine that is executed by the system of the first embodiment.

Next, specific processing of the offset error correction of the humidity sensor that is executed in the system of the first embodiment will be described. FIG. 8 is a flowchart of a routine that is executed by the system of the first embodiment. Note that the routine illustrated in FIG. 8 is a routine for performing the offset error correction of the humidity sensor, and is executed by the ECU 70 at the time of start of the engine 10, for example.

In the routine illustrated in FIG. 8, an intake air temperature T0 at an initial stage is acquired by the temperature sensor 74 first (step S2). Next, the relative humidity RHi (i=1, 2, . . . ) and the intake air temperature Ti at present are acquired (step S4). Here, specifically, a value obtained by adding a humidity correction value that will be described later to the sensor value (the relative humidity) of the humidity sensor 76 is acquired as the relative humidity RHi. Further, in the present step, at the time of acquiring the relative humidity RHi, the intake air temperature Ti that is detected by the temperature sensor 74 is acquired.

Next, increment processing of i to i+1 is performed (step S6). Next, it is determined whether or not an absolute value of a difference between the present intake air temperature Ti which is acquired in the processing of the latest step S4 and the intake air temperature T0 at the initial stage which is acquired in the processing in step S2 described above is larger than a threshold value (step S8). As for the threshold value in this case, a value set in advance is read as the temperature difference in the intake air temperature that enables to determine the offset error of the humidity sensor. When establishment of |Ti−T0|>threshold value is not recognized as a result, the flow shifts to the processing in step S4 again. Subsequently, acquisition of the intake air temperature Ti and the relative humidity RHi (i=1, 2, . . . ) is repeatedly performed until establishment of determination of |Ti−T0|>threshold value is recognized.

When establishment of |Ti−T0|>threshold value is recognized in step S8 described above, the flow shifts to a next step, and the absolute humidity AHi (i=1, 2, . . . , n) at the time of the intake air temperature Ti and the relative humidity RHi (i=1, 2, . . . , n) is each calculated (step S10).

Figure 9:
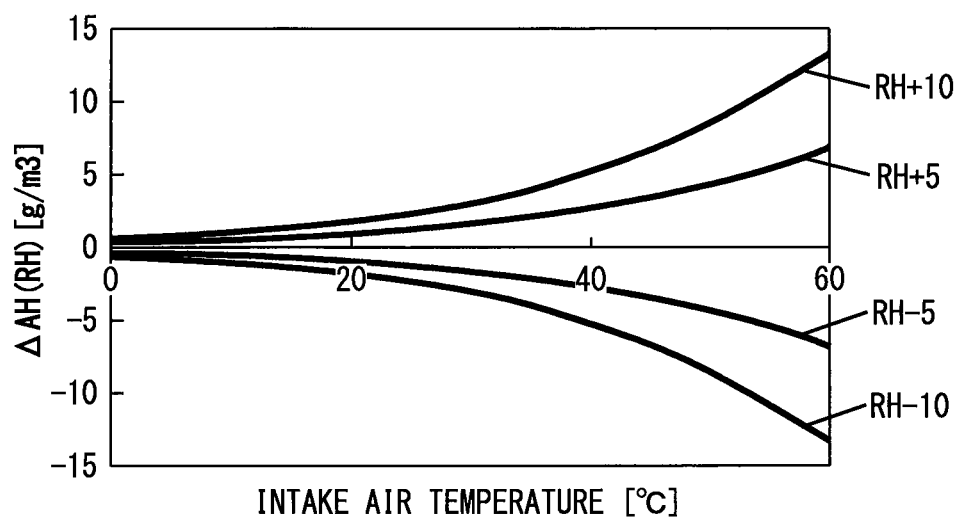
FIG. 9 is a diagram illustrating a relationship of a change amount $\Delta AHi, j$ to an intake air temperature $Ti$, at each $\Delta RHj$.

Next, the change amount ΔAHi, j (ΔRHj, Ti) of the absolute humidity AHi in the case of the relative humidity RHi changing by ΔRHj (=0, ±5, ±10, . . . ) at the intake air temperature Ti is calculated (step S12). Note that ΔRHj is a value for changing the relative humidity RHi to a plus side or a minus side, and is set in such a manner as to be ΔRH1=0, ΔRH2=+5, ΔRH3=−5, ΔRH4=+10, ΔRH5=−10, . . . , ΔRHm= . . . (j=1, 2, . . . , m), for example. FIG. 9 is a diagram illustrating a relationship of the change amount ΔAHi, j to the intake air temperature Ti at each ΔRHj. Here, by using a function or a map in which the relationship illustrated in FIG. 9 is set, the change amount ΔAHi, j corresponding to the intake air temperature Ti and ΔRHj is calculated.

Next, the absolute humidity AHi, j (i=1, 2, . . . , n; j=1, 2, . . . , m) that is a result of adding the change amount ΔAHi, j (ΔRHj, Ti) to the absolute humidity AHi is calculated, and the variance value Vj from an average of the absolute humidities AHi, j is calculated (step S14). Next, ΔRHj with which the variance value Vj becomes minimum is calculated, and the ΔRHj is determined as a deviation ΔRH between the true value and the detection value of the relative humidity (step S16).

Next, presence or absence of establishment of the deviation ΔRH<threshold value is determined (step S18). When the deviation ΔRH is excessively large, some error detection is likely to be included in the process until the deviation ΔRH is calculated. As for the threshold value, a value that is set in advance as the threshold value for determining whether or not the deviation ΔRH includes error detection is read. When establishment of ΔRH<threshold value is not recognized as a result, the flow shifts to a next step, and it is determined that ΔRH which is calculated this time is based on error detection (step S20). Subsequently, in the routine of this time, the humidity correction amount is not newly calculated, and the present routine is ended.

Meanwhile, when establishment of ΔRH<threshold value is recognized in step S18 described above, a value ΔRH' that is obtained by multiplying ΔRH by a predetermined gradual change amount is calculated (step S22). The predetermined gradual change amount is a value for restricting ΔRH to a predetermined ratio to restrain an abrupt change of the humidity correction amount that will be described later, and a positive value which is 1 or less that is set in advance is used.

Next, the humidity correction amount in the routine of this time is calculated (step S24). Here, minimum value selection is performed between a predetermined correction amount limitation and the deviation ΔRH' calculated in step S22 described above. The predetermined correction amount limitation is a value for fixing an allowable maximum value of the deviation ΔRH' to restrain an abrupt change of the humidity correction amount that will be described later, and a value that is set in advance is used. Note that the processing from steps S18 to S24 described above is not indispensable, and therefore may be skipped.

Next, a final humidity correction amount is calculated (step S26). Here, the final humidity correction amount is calculated by adding the humidity correction amount of this time that is calculated in step S24 described above to the humidity correction amount in the routine of the previous time.

As described above, according to the system of the first embodiment, it becomes possible to correct the sensor value that is detected by the humidity sensor 76 which is provided in the intake passage 22 and bring the sensor value close to the true value with high precision.

Incidentally, in the system of the aforementioned first embodiment, the deviation ΔRH for the variation degree of the absolute humidity AHi, j to be small is calculated by using the variance value Vj from the average of the absolute humidities AHi, j (i=1, 2, . . . , n; j=1, 2, . . . , m). However, the method for calculating the deviation ΔRH is not limited to the method that uses the variance value Vj, but the deviation ΔRH may be calculated by determining the variation degree of the absolute humidities AHi, j by using another known estimation function or the like.

In the system of the first embodiment described above, the humidity correction amount corresponds to a "correction value" of a first disclosure, and the controller 701 corresponds to a "controller" of the first disclosure.

Second Embodiment

Next, a second embodiment of the present disclosure will be described with reference to the drawings. The system of the second embodiment is realized by causing the ECU 70 to execute a routine illustrated in FIG. 10 by using a hardware configuration similar to the hardware configuration in the first embodiment.

2-1. Operation of System of Second Embodiment

The system of the second embodiment of the present disclosure differs from the system of the first embodiment in procedure of calculating the variance value $V_j$. That is, in the system of the second embodiment of the present disclosure, the relative humidities $RH_i$ are respectively calculated from the sensor values at the intake air temperatures $T_i$ ($i=1, 2, \ldots, n$). Subsequently, the absolute humiditis $AH_{i,j}$ of the values obtained by adding $\Delta RH_j$ ($j=1, 2, \ldots, m$) to the respective relative humidities $RH_i$ which are calculated are respectively calculated, and the variance value $V_j$ of them are calculated.

The offset error correction of the humidity sensor 76 in the system of the second embodiment is realized by the controller 701 illustrated in FIG. 7 which is similar to the controller in the system of the first embodiment. In the offset error correction of the humidity sensor by comparison of the absolute humidities described above, the intake air temperature in FIG. 7 corresponds to the intake air temperature $T_i$ ($i=1, 2, \ldots, n$), the sensor value corresponds to the relative humidity $RH_i$ ($i=1, 2$), and the humidity index value corresponds to the absolute humidity $AH_{i, j}$.

2-2. Specific Processing of System of Second Embodiment

Figure 10:
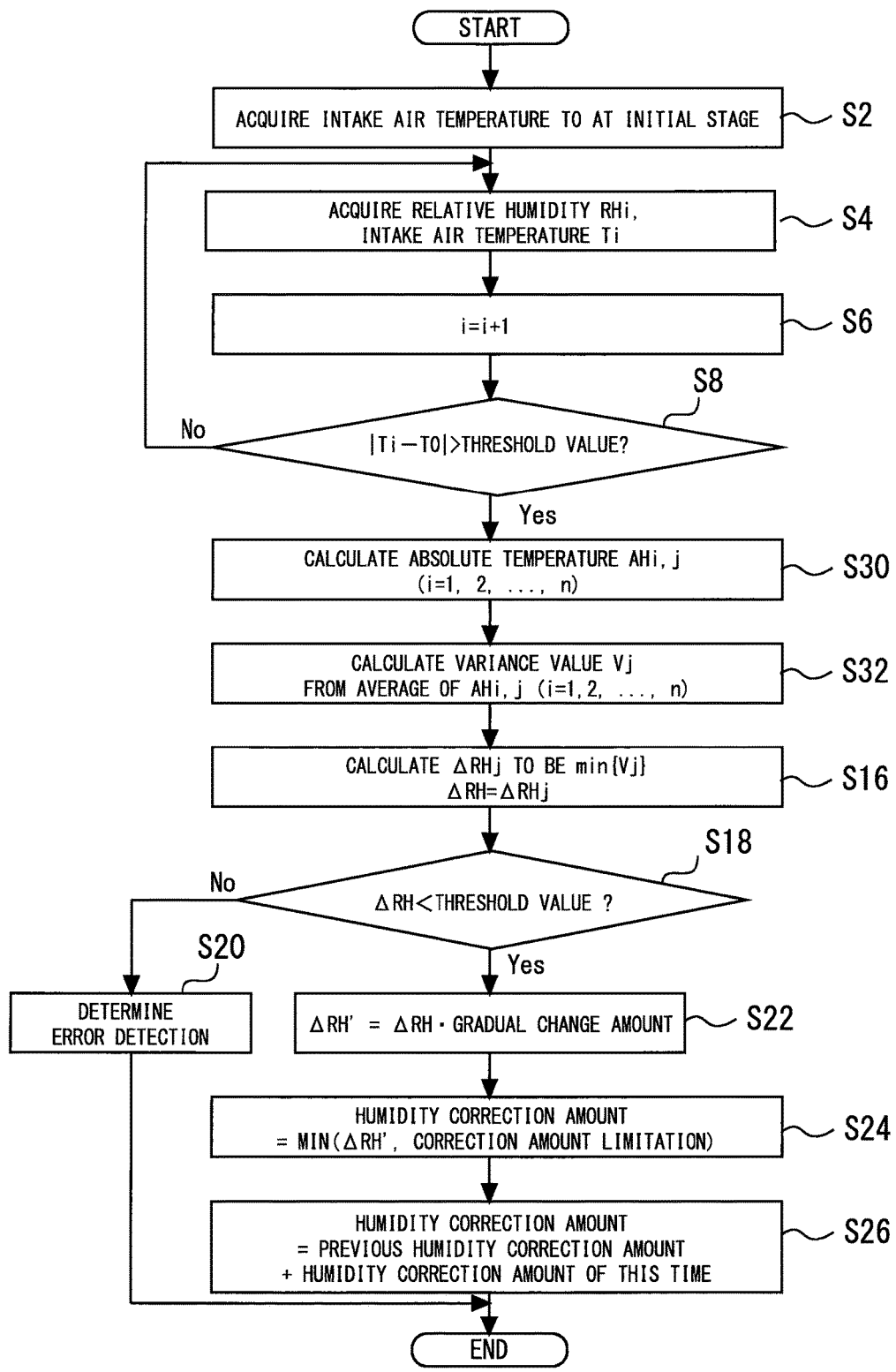
FIG. 10 is a flowchart of a routine that is executed by a system of a second embodiment.

Next, specific processing of the offset error correction of the humidity sensor that is executed in the system of the second embodiment will be described. FIG. 10 is a flowchart of a routine that is executed by the system of the second embodiment. The routine illustrated in FIG. 10 is a routine for performing the offset error correction for the humidity sensor, and is executed by the ECU 70 at the time of start of the engine 10, for example.

In steps S2, S4, S6 and S8 of the routine illustrated in FIG. 10, similar processing to the processing in steps S2, S4, S6 and S8 of the routine illustrated in FIG. 8 is executed. When establishment of step S8 is recognized, the flow shifts to a next step.

In the next step, the absolute humidities $AH_{i,j}$ in the case of the relative humidities $RH_i$ changing by $\Delta RH_j$ ($=0, \pm 5, \pm 10, \ldots$) at the intake air temperatures $T_i$ ($i=1, 2, \ldots, n$) are calculated (step S30). Next, the variance value $V_j$ from the average of the absolute humidities $AH_{i,j}$ ($i=1, 2, \ldots, n; j=1, 2, \ldots, m$) is calculated (step S32).

When the processing in step S32 described above is executed, the flow shifts to processing in step S16 next. In steps S16 to S26, processing similar to the processing in steps S16 to S26 of the routine illustrated in FIG. 8 is executed.

As described above, according to the system of the second embodiment, it becomes possible to correct the sensor value detected by the humidity sensor 76 provided in the intake passage 22 to bring the sensor value close to the true value with high precision.

Third Embodiment

Next, a third embodiment of the present disclosure will be described with reference to the drawings. A system of the third embodiment is realized by causing the ECU 70 to execute a routine illustrated in FIG. 11 that will be described later by using a hardware configuration similar to the hardware configuration in the first embodiment.

3-1. Operation of System of Third Embodiment

The system of the third embodiment of the present disclosure differs from the system of the second embodiment in a feature of using relative humidity at a predetermined reference intake air temperature that is converted from absolute humidity as a humidity index value. That is, in the system of the third embodiment of the present disclosure, relative humidities $RH_{i, j}$ ($AH_{i, j}, Ta$) at a predetermined reference intake air temperature Ta are respectively calculated from the absolute humidities $AH_{i, j}$ ($i=1, 2, \ldots, n; j=1, 2, \ldots, m$), and the variance value $V_j$ thereof is calculated.

The offset error correction of the humidity sensor 76 in the system of the third embodiment is realized by the controller 701 illustrated in FIG. 7 as in the system of the first embodiment. In the offset error correction of the humidity sensor by comparison of the absolute humidities described above, the intake air temperature in FIG. 7 corresponds to the intake air temperature $T_i$ ($i=1, 2, \ldots, n$), the sensor value corresponds to the relative humidity $RH_i$ ($i=1, 2, \ldots, n$), and the humidity index value corresponds to the relative humidity $RH_{i, j}$ ($AH_{i, j}, Ta$).

3-2. Specific Processing of System of Third Embodiment

Figure 11:
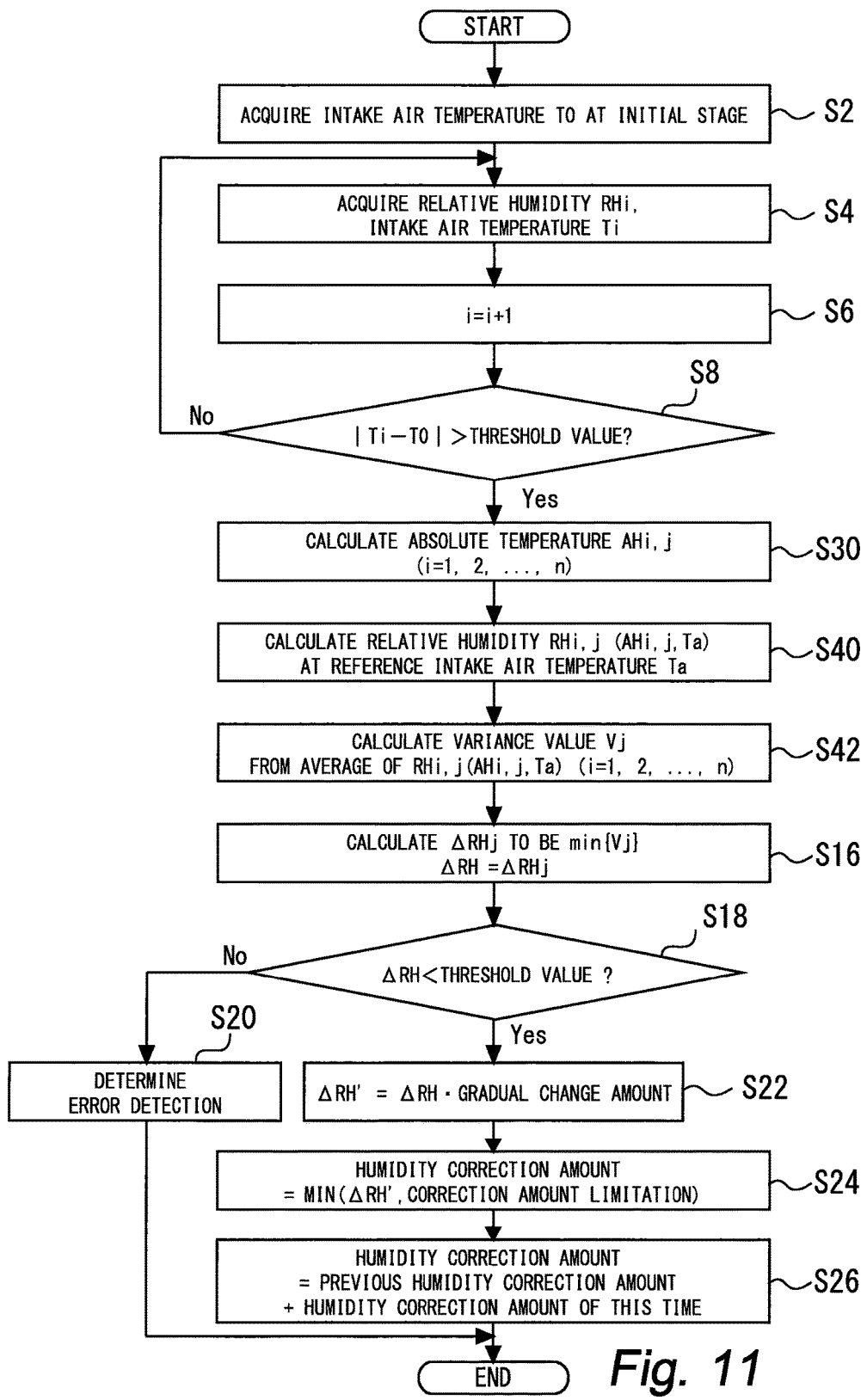
FIG. 11 is a flowchart of a routine that is executed by a system of a third embodiment.

Next, specific processing of the offset error correction of the humidity sensor that is executed in the system of the third embodiment will be described. FIG. 11 is a flowchart of a routine that is executed by the system of the third embodiment. The routine illustrated in FIG. 11 is a routine for performing the offset error correction of the humidity sensor, and is executed by the ECU 70 at the time of start of the engine 10, for example.

In steps S2, S4, S6, S8 and S30 of the routine illustrated in FIG. 11, processing similar to the processing in steps S2, S4, S6, S8 and S30 of the routine illustrated in FIG. 10 is executed. Subsequently, in a next step to the processing in step S30, the relative humidities $RH_{i, j}$ ($AH_{i, j}, Ta$) ($i=1, 2, \ldots, n; j=1, 2, \ldots, m$) in the case of the intake air temperature being the reference intake air temperature Ta are calculated, from respective equal absolute humidity lines of the absolute humidities $AH_{i, j}$ calculated in step S30 described above (step S40). Next, the variance value $V_j$ from an average of the relative humidities $RH_{i, j}$ ($AH_{i, j}, Ta$) is calculated (step S42).

When the processing in step S42 described above is executed, the flow shifts to processing in step S16 next. In steps S16 to S26, processing similar to the processing in steps S16 to S26 of the routine illustrated in FIG. 10 is executed.

As described above, according to the system of the third embodiment, the relative humidities that are detected at different intake air temperatures are converted into the relative humidities at the same intake air temperature, and thereafter are compared, so that it becomes possible to correct the relative humidity detected by the humidity sensor 76 with high precision and bring the relative humidity close to the true value.

Fourth Embodiment

Next, a fourth embodiment of the present disclosure will be described with reference to the drawings. The system of the fourth embodiment is realized by causing the ECU 70 to execute a routine illustrated in FIG. 12 that will be described later by using a hardware configuration similar to the hardware configuration in the first embodiment.

4-1. Operation of System of Fourth Embodiment

The system of the fourth embodiment of the present disclosure has a feature in an operation of determining $\Delta RH_j$ with which the absolute humidities $AH_{i, j}$ at arbitrary two different points of the intake air temperature (for example, $AH_{1, j}$ and $AH_{2, j}$) among the absolute humidities $AH_{i, j}$, have the same value, as the deviation $\Delta RH$, without using the variance value $V_j$ of the absolute humidities $AH_{i, j}$. That is, in the system of the fourth embodiment of the present disclosure, the absolute humidity $AH_{1, j}$ ($j=1, 2, \ldots, m$) at a time of $i=1$, and absolute humidity $AH_{2, j}$ ($j=1, 2, \ldots, m$)

at a time of i=2, for example, are calculated, and ΔRHj with which AH1, j=AH2, j is established is calculated as the deviation ΔRHj.

The offset error correction of the humidity sensor 76 in the system of the fourth embodiment is realized by the controller 701 illustrated in FIG. 7 as in the system of the first embodiment. In the offset error correction of the humidity sensor by comparison of the absolute humidities described above, the intake air temperature in FIG. 7 corresponds to the intake air temperature Ti (i=1, 2), the sensor value corresponds to the relative humidity RHi (i=1, 2), and the humidity index value corresponds to the absolute humidity AHi, j (i=1, 2; j=1, 2, . . . , m).

4-2. Specific Processing of System of Fourth Embodiment

Figure 12:
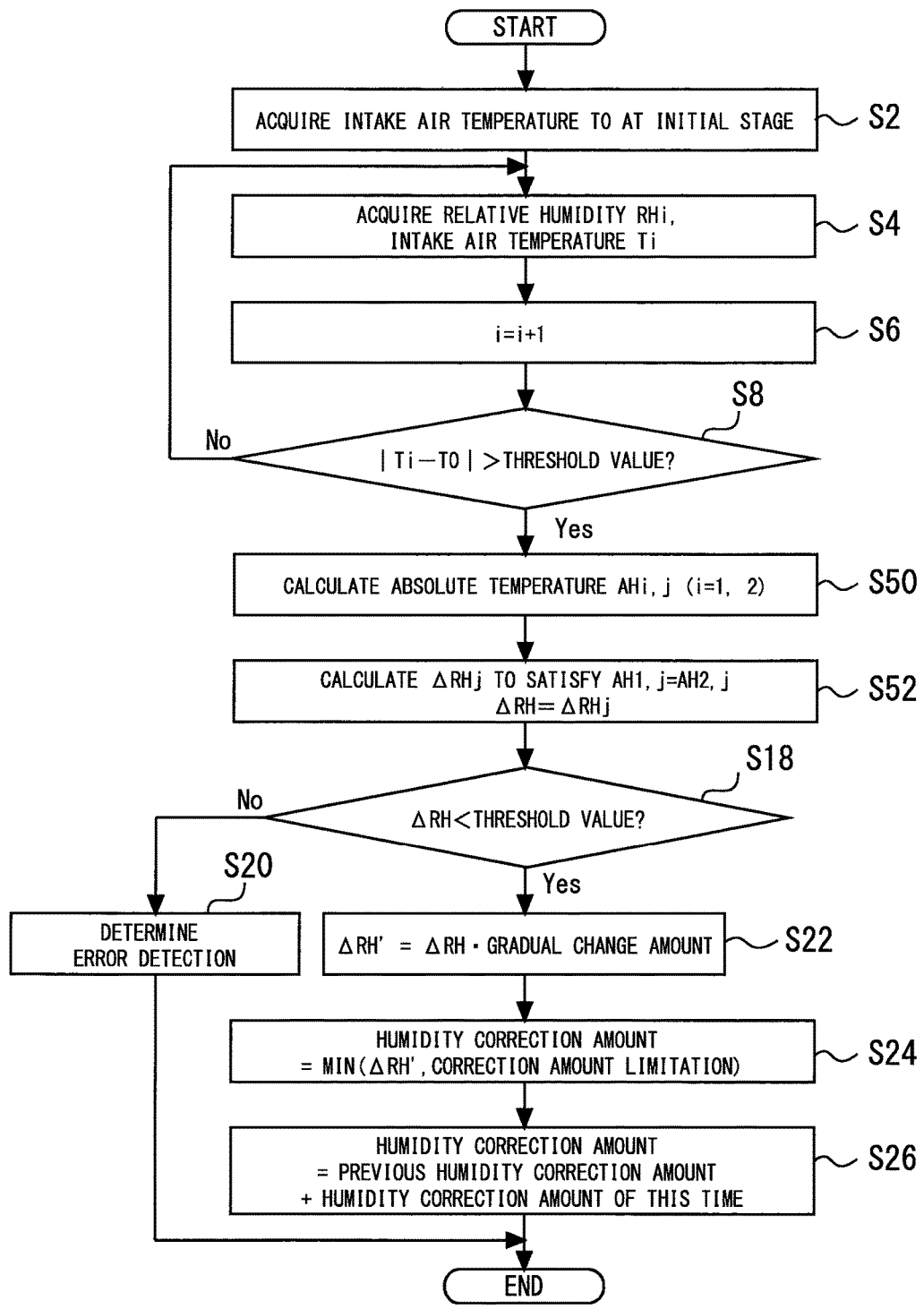
FIG. 12 is a flowchart of a routine that is executed by a system of a fourth embodiment.

Next, specific processing of the offset error correction of the humidity sensor that is executed in the system of the fourth embodiment will be described. FIG. 12 is a flowchart of a routine that is executed by the system of the fourth embodiment. The routine illustrated in FIG. 12 is a routine for performing the offset error correction of the humidity sensor, and is executed by the ECU 70 at the time of start of the engine 10, for example.

In steps S2, S4, S6 and S8 of the routine illustrated in FIG. 12, processing similar to the processing in steps S2, S4, S6 and S8 of the routine illustrated in FIG. 10 is executed. When establishment of step S8 is recognized, the flow shifts to a next step.

In the next step, the absolute humidities AHi, j (j=1, 2, . . . , m) in the case of the relative humidity RHi changing by ΔRHj at the intake air temperatures Ti (i=1, 2) are calculated (step S50). Next, ΔRHj with which the calculated absolute humidity AH1, j=AH2, j is established is calculated, and the ΔRHj is determined as the deviation ΔRH between the true value and the detection value of the relative humidity (step S52).

When the processing in step S52 described above is executed, the flow shifts to processing in step S18 next. In steps S18 to S26, processing similar to the processing in steps S18 to S26 of the routine illustrated in FIG. 10 is executed.

As described above, according to the system of the fourth embodiment, it becomes possible to correct the relative humidity detected by the humidity sensor 76 with high precision to bring the relative humidity close to the true value without performing a complicated arithmetic operation.

Incidentally, in the system of the fourth embodiment described above, ΔRHj with which the absolute humidity AH1, j=absolute humidity AH2, j is established is calculated. However, a calculation method of ΔRHj is not limited to this, and ΔRHj can be calculated so that a difference value of the absolute humidity AH1, j and the absolute humidity AH2, j is close to zero.

In the system of the fourth embodiment described above, the intake air temperature Ti (i=1) corresponds to a "first intake air temperature" in a fifth disclosure, and the intake air temperature Ti (i=2) corresponds to a "second intake air temperature" in the fifth disclosure. The relative humidity RHi (i=1) corresponds to a "first sensor value" in the fifth disclosure, and the relative humidity RHi (i=2) corresponds to a "second sensor value" in the fifth disclosure. The absolute humidity AHi, j (i=1; j=1, 2, . . . , m) corresponds to a "first humidity index value" in the fifth disclosure, and the absolute humidity AHi, j (i=2; j=1, 2, . . . , m) corresponds to a "second humidity index value" in the fifth disclosure.

Fifth Embodiment

Next, a fifth embodiment of the present disclosure will be described with reference to the drawings. The system of the fifth embodiment is realized by causing the ECU 70 to execute a routine illustrated in FIG. 13 that will be described later by using a hardware configuration similar to the hardware configuration in the first embodiment.

5-1. Operation of System of Fifth Embodiment

The system of the fifth embodiment of the present disclosure has a feature in an operation of converting the absolute humidities AHi, j at arbitrary two different points of the intake air temperature (for example, AH1, j and AH2, j) among the absolute temperatures AHi, j, into relative humidities at the reference intake air temperature Ta, and determining ΔRHj, with which the relative humidities after conversion have the same value, as the deviation ΔRH, without using the variance value Vj of the absolute humidities AHi, j. That is, in the system of the fifth embodiment of the present disclosure, the absolute humidity AH1, j (j=1, 2, . . . , m) at a time of i=1, and absolute humidity AH2, j (j=1, 2, . . . , m) at a time of i=2, for example, are calculated. Subsequently, by using the equal absolute humidity line of the absolute humidities AH1, j and AH2, j, the relative humidities RH1, j (AH1, j, Ta) and RH1, j (AH1, j, Ta) in the predetermined reference intake air temperature Ta are respectively calculated, and ΔRHj with which RH1, j (AH1, j, Ta)=RH1, j (AH1, j, Ta) is established is calculated as the deviation ΔRHj.

Offset error correction of the humidity sensor 76 in the system of the fifth embodiment is realized by the controller 701 illustrated in FIG. 7 as in the system of the first embodiment. In the offset error correction of the humidity sensor by comparison of the absolute humidities described above, the intake air temperature in FIG. 7 corresponds to the intake air temperature Ti (i=1, 2), the sensor value corresponds to the relative humidity RHi (i=1, 2), and the humidity index value corresponds to the relative humidity RHi, j (AHi, j, Ta) (n=1, 2; j=1, 2, . . . , m).

5-2. Specific Processing of System of Fifth Embodiment

Figure 13:
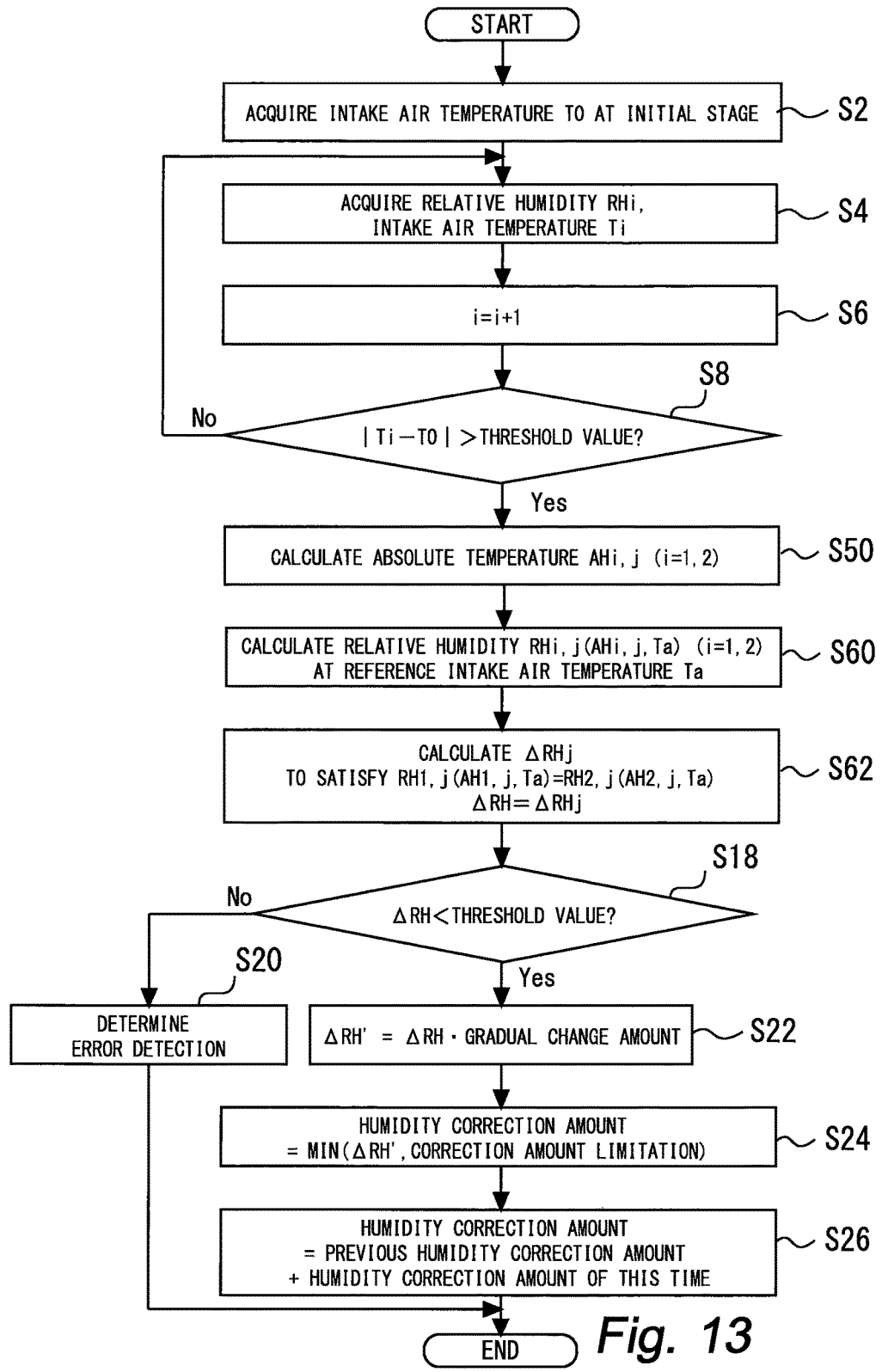
FIG. 13 is a flowchart of a routine that is executed by a system of a fifth embodiment.

Next, specific processing of the offset error correction of the humidity sensor that is executed in the system of the fifth embodiment will be described. FIG. 13 is a flowchart of a routine that is executed by the system of the fifth embodiment. The routine illustrated in FIG. 13 is a routine for performing the offset error correction of the humidity sensor, and is executed by the ECU 70 at the time of start of the engine 10, for example.

In steps S2, S4, S6, S8 and S50 of the routine illustrated in FIG. 13, processing similar to the processing in steps S2, S4, S6, S8 and S50 of the routine illustrated in FIG. 12 is executed. Subsequently, in a next step to the processing in step S50, the relative humidities RHi, j (AHi, j, Ta) (i=1, 2; j=1, 2, . . . , m) in the case of the intake air temperature being the reference intake air temperature Ta are calculated (step S60) from the respective equal absolute humidity lines of the absolute humidities AHi, j (i=1, 2) calculated in step S50 described above. Next, ΔRHj with which the calculated relative humidity RH1, j (AH1, j, Ta)=RH2, j (AH2, j, Ta) is established is calculated, and the ΔRHj is determined as the deviation ΔRH between the true value and the detection value of the relative humidity (step S62).

When the processing in step S62 described above is executed, the flow shifts to processing in step S18 next. In steps S18 to S26, processing similar to the processing in steps S18 to S26 of the routine illustrated in FIG. 12 is executed.

As described above, according to the system of the fifth embodiment, it becomes possible to correct the relative humidity detected by the humidity sensor 76 with high precision to bring the relative humidity close to the true value without performing a complicated arithmetic operation.

Incidentally, in the system of the fifth embodiment described above, ΔRHj with which the relative humidity RH1, j (AH1, j, Ta)=absolute humidity RH2, j (AH2, j, Ta) is established is calculated. However, a calculation method of ΔRHj is not limited to this, and ΔRHj can be calculated so that the difference value of the relative humidity RH1, j (AH1, j, Ta) and the relative humidity RH2, j (AH2, j, Ta) is close to zero.

In the system of the fifth embodiment described above, the intake air temperature Ti (i=1) corresponds to the "first intake air temperature" in the fifth disclosure, and the intake air temperature Ti (i=2) corresponds to the "second intake air temperature" in the fifth disclosure. The relative humidity RHi (i=1) corresponds to the "first sensor value" in the fifth disclosure, and the relative humidity RHi (i=2) corresponds to a "second sensor value" in the fifth disclosure. The relative humidity RH1, j (AH1, j, Ta) corresponds to the "first humidity index value" in the fifth disclosure, and the relative humidity RH2, j (AH2, j, Ta) corresponds to the "second humidity index value" in the fifth disclosure.

Sixth Embodiment

Next, a sixth embodiment of the present disclosure will be described with reference to the drawing. The system of the sixth embodiment is realized by causing the ECU 70 to execute a routine illustrated in FIG. 14 that will be described later by using a hardware configuration similar to the hardware configuration in the first embodiment.

6-1. Operation of System of Sixth Embodiment

The system of the sixth embodiment of the present disclosure differs from the system in the first embodiment in a feature of using a relative humidity difference e_i (AHj) from the relative humidity RHi (TI) (i=1, 2, ..., n) to the predetermined reference absolute humidity AHj (j=1, 2, ..., m) as the humidity index value. That is, in the system of the sixth embodiment of the present disclosure, relative humidities RH_AHj (Ti) (i=1, 2, ..., n) corresponding to the reference absolute humidity AHj (j=1, 2, ..., m) at the intake air temperature Ti are respectively calculated. Subsequently, the relative humidities RHi are subtracted from the calculated relative humidities RH_ AHj (Ti), whereby the relative humidity differences e_i (AHj) are respectively calculated, and a variance value V (AHj) thereof is calculated.

The variance value V (AHj) represents a variation degree of the relative humidity differences e_i (AHj), and therefore, the reference absolute humidity AH corresponding to a point at which the variance value V (AHj) becomes minimum can be determined as the absolute humidity which is the closest to the true value. Accordingly, in the system of the sixth embodiment of the present disclosure, the reference absolute humidity AH is calculated from the variance value V (AHj), and an average value of the relative humidity differences e_i (AH) (i=1, 2, ..., n) from the reference absolute humidity AH is calculated as the deviation ΔRH.

Offset error correction of the humidity sensor 76 in the system of the sixth embodiment is realized by the controller 701 illustrated in FIG. 7 as in the system of the first embodiment. In the offset error correction of the humidity sensor by using the aforementioned relative humidity difference e_i (AHj), the intake air temperature in FIG. 7 corresponds to the intake air temperature Ti (i=1, 2, ..., n), the sensor value corresponds to the relative humidity RHi (i=1, 2, ..., n), and the humidity index value corresponds to the relative humidity difference e_i (AHj) (i=1, 2, ..., n; j=1, 2, ..., m).

6-2. Specific Processing of System of Sixth Embodiment

Figure 14:
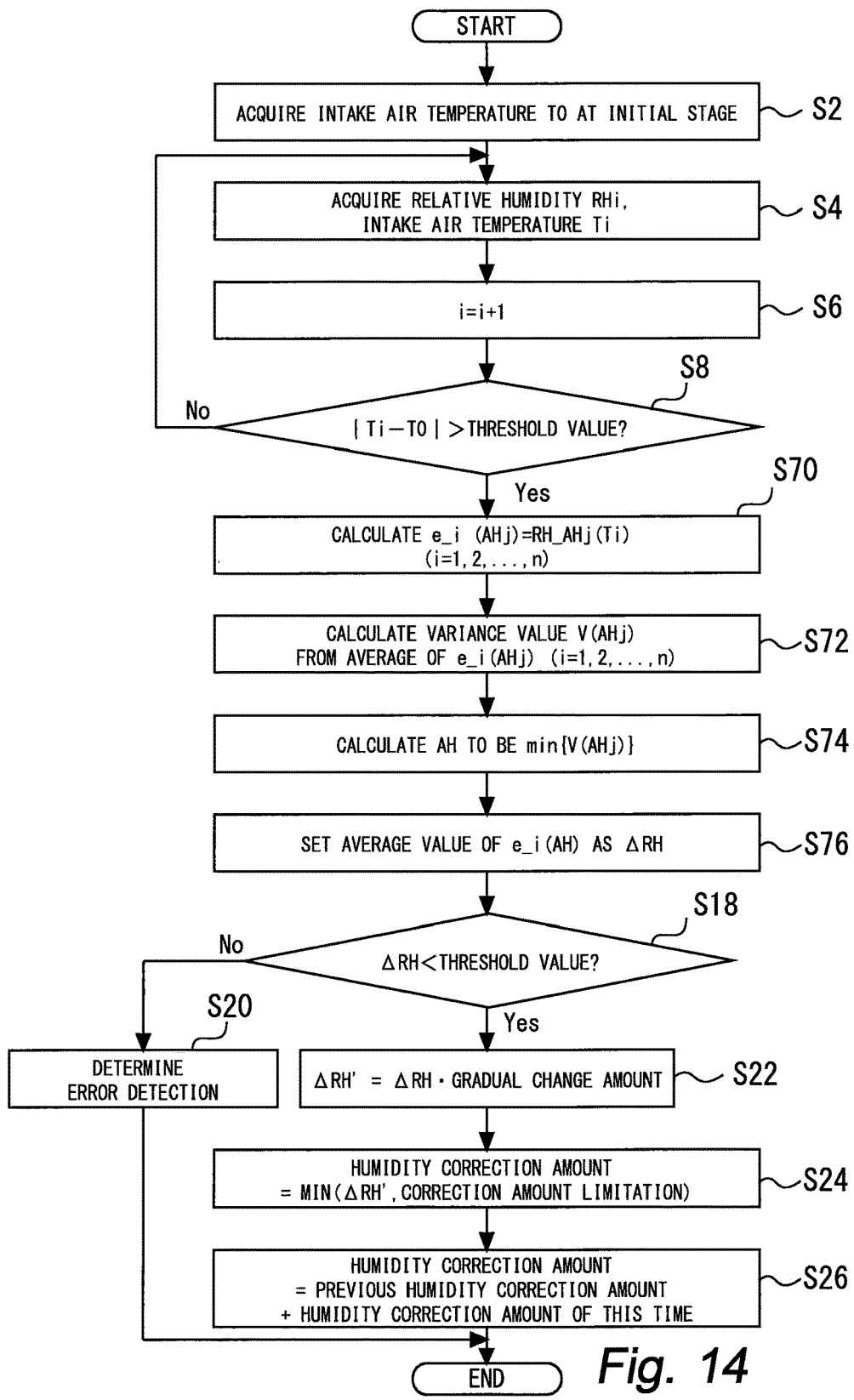
FIG. 14 is a flowchart of a routine that is executed by a system of a sixth embodiment.

Next, specific processing of the offset error correction of the humidity sensor that is executed in the system of the sixth embodiment will be described. FIG. 14 is a flowchart of a routine that is executed by the system of the sixth embodiment. The routine illustrated in FIG. 14 is a routine for performing the offset error correction of the humidity sensor, and is executed by the ECU 70 at the time of start of the engine 10, for example.

In steps S2, S4, S6, and S8 of the routine illustrated in FIG. 14, processing similar to the processing in steps S2, S4, S6, and S8 of the routine illustrated in FIG. 8 is executed. Subsequently, when establishment of step S8 is recognized, the flow shifts to a next step.

In the next step, the relative humidity difference e_i (AHj) from the relative humidity RHi at the intake air temperature Ti (i=1, 2, ..., n) to the reference absolute humidity AHj (j=1, 2, ..., m) is calculated (step S70). The ECU 70 stores the relative humidity RHi at the time of the reference absolute humidity AHj (j=1, 2, ..., m) as a function RH_AHj (Ti) (i=1, 2, ..., n) of the intake air temperature Ti. Here, the relative humidity differences e_i (AHj) are respectively calculated by subtracting the relative humidities RHi from the calculated relative humidities RH_AHj (Ti).

Next, the variance value V (AHj) from an average of the relative humidity differences e_i (AHj) (i=1, 2, ..., n; j=1, 2, ..., m) is calculated (step S72). Next, AH at which the variance value V (AHj) becomes minimum is calculated, and the AH is determined as a value that is the closest to the true value of the absolute humidity (step S74). Next, the average value of the relative humidity differences e_i (AH) (i=1, 2, ..., n) is calculated, and the average value is determined as the deviation ΔRH (step S76).

When the processing in step S76 described above is executed, the flow shifts to processing in step S18 next. In steps S18 to S26, processing similar to the processing in steps S18 to S26 of the routine illustrated in FIG. 8 is executed.

As described above, according to the system of the sixth embodiment, it becomes possible to correct the sensor value detected by the humidity sensor 76 provided in the intake passage 22 to bring the sensor value close to the true value with high precision.

Incidentally, in the system of the sixth embodiment described above, the absolute humidity AH at which the variance value V (AHj) from the average of the relative humidity differences e_i (AHj) (i=1, 2, ..., n; j=1, 2, ..., m) becomes minimum is calculated as the reference absolute humidity AH which is the closest to the true value. However, a method for calculating the reference absolute humidity AH from the variance value V (AHj) is not limited to this, but the absolute humidity AH at the time of the variance value V (AHj) becoming zero may be calculated by using a known arithmetic operation method such as a trigonometry and a steepest descent method, and the absolute humidity AH may be determined as the reference absolute humidity AH. Further, the method for calculating the reference absolute humidity AH is not limited to the method using the variance value V (AHj), but a variation degree of the relative humidity differences e_i (AHj) may be determined by using another known estimation function or the like to calculate the reference absolute humidity AH.

In the system of the sixth embodiment described above, the reference absolute humidity AH corresponds to "reference absolute humidity" in a sixth disclosure, and the relative humidity difference e_i (AHj) corresponds to a "relative humidity difference" in the sixth disclosure.

What is claimed is:

1. A control apparatus for an internal combustion engine comprising:
   a humidity sensor that is disposed in an intake passage of the internal combustion engine, and is configured to detect a sensor value corresponding to relative humidity of intake air in the intake passage;
   a temperature sensor configured to detect an intake air temperature in a position of the humidity sensor; and
   a controller configured to correct an offset error of the sensor value by performing correction by adding a correction value to the sensor value,
   the controller being configured to:
   acquire the intake air temperatures at a plurality of timings in a process of the intake air temperature changing;
   acquire the sensor values at the respective plurality of timings;
   calculate respective humidity index values that are not dependent on influences of temperature differences of the intake air temperatures using values obtained by adding respective relative humidity change amounts to the respective sensor values;
   determine the relative humidity change amount that causes a variation degree of the humidity index values to become small; and
   set the determined relative humidity change amount as the correction value,
   wherein the control apparatus controls the internal combustion engine using sensor values that are corrected by adding the correction value.

2. The control apparatus for the internal combustion engine according to claim 1,
   wherein the controller is configured to calculate absolute humidity values as the respective humidity index values which are calculated by using the values obtained by adding the respective relative humidity change amounts to the respective sensor values and the intake air temperature corresponding to the respective sensor values.

3. The control apparatus for the internal combustion engine according to claim 1,
   wherein the controller is configured to calculate relative humidity values at a time of the intake air temperature being a predetermined reference intake air temperature as the respective humidity index values by using the values obtained by adding the respective relative humidity change amounts to the respective sensor values.

4. The control apparatus for the internal combustion engine according to claim 1,
   wherein the controller is configured to determine the correction value so that the variance degree of the humidity index values becomes minimum.

5. The control apparatus for the internal combustion engine according to claim 1,
   wherein the controller is configured to:
   during the acquiring of the intake air temperatures at a plurality of timings and the acquiring of the sensor values at the respective plurality of timings, acquire a first sensor value that is the sensor value at a time of the intake air temperature being a first intake air temperature, and a second sensor value that is the sensor value at a time of the intake air temperature changing from the first intake air temperature and reaching a second intake air temperature,
   during the calculating of the respective humidity index values, calculate values that are not dependent on an influence of a temperature difference of the first intake air temperature and the second intake air temperature using values obtained by adding respective relative humidity change amounts to the first sensor value and the second sensor value, as first humidity index values and second humidity index values respectively, and
   during the determining of the relative humidity change amount and the setting of the determined relative humidity change amount, determine the relative humidity change amount that causes a difference value of a corresponding one of the first humidity index values and the second humidity index values to be close to zero and set the determined relative humidity change amount as the correction value.

6. The control apparatus for the internal combustion engine according to claim 1,
   wherein the controller is configured to restrict acquisition of the sensor value, until an integrated value of a volume of intake air that is taken into the intake passage after start of the internal combustion engine exceeds a capacity from an inlet to the humidity sensor in the intake passage, in a warm-up period of the internal combustion engine.

7. The control apparatus for the internal combustion engine according to claim 1,
   wherein the controller is configured to restrict acquisition of the sensor value, when intake air containing a fuel component flows in the position of the humidity sensor in the intake passage of the internal combustion engine.

8. A control apparatus for an internal combustion engine comprising:
   a humidity sensor that is disposed in an intake passage of the internal combustion engine, and is configured to detect a sensor value corresponding to relative humidity of intake air in the intake passage;
   a temperature sensor configured to detect an intake air temperature in a position of the humidity sensor; and
   a controller configured to correct an offset error of the sensor value by performing correction by adding a correction value to the sensor value,
   the controller being configured to
   acquire the intake air temperatures at a plurality of timings in a process of the intake air temperature changing;
   acquire the sensor values at the respective plurality of timings;
   calculate respective relative humidity differences between relative humidity values calculated using respective reference absolute humidity values and relative humidity values calculated using the sensor values as respective humidity index values, and
   calculate the reference absolute humidity value at which a variation degree of the relative humidity differences becomes minimum, and
   set an average value of the relative humidity differences at the calculated reference absolute humidity as the correction value,
   wherein the control apparatus controls the internal combustion engine using sensor values that are corrected by adding the correction value.

9. A control apparatus for an internal combustion engine comprising:
- a humidity sensor that is disposed in an intake passage of the internal combustion engine, and is configured to detect a sensor value corresponding to relative humidity of intake air in the intake passage;
- a temperature sensor configured to detect an intake air temperature in a position of the humidity sensor; and
- a controller configured to correct an offset error of the sensor value by performing correction by adding a correction value to the sensor value, the controller being configured to:
- acquire the intake air temperatures at a plurality of timings in a process of the intake air temperature changing;
- acquire the sensor values at the respective plurality of timings;
- calculate respective absolute humidities by using the respective sensor values and the intake air temperatures corresponding to the respective sensor values;
- calculate respective humidity index values obtained by adding absolute humidity change amounts calculated from respective relative humidity change amounts to the respective absolute humidities;
- determine the absolute humidity change amounts that cause a variation degree of the humidity index values to become small; and
- set the relative humidity change amount used to calculate the determined absolute humidity change amounts as the correction value, wherein the control apparatus controls the internal combustion engine using the sensor values that are corrected by adding the correction value.

* * * * *